United States Patent [19]

Buican et al.

[11] Patent Number: 5,117,466
[45] Date of Patent: May 26, 1992

[54] INTEGRATED FLUORESCENCE ANALYSIS SYSTEM

[75] Inventors: Tudor N. Buican; Thomas M. Yoshida, both of Los Alamos, N. Mex.

[73] Assignee: The United States of America as represented by the United States Department of Energy, Washington, D.C.

[21] Appl. No.: 693,466

[22] Filed: Apr. 30, 1991

[51] Int. Cl.⁵ .............................................. G06K 9/00
[52] U.S. Cl. ...................................... 382/6; 382/17; 356/73; 356/318; 356/346; 356/417; 250/458.1; 250/461.2
[58] Field of Search ............... 356/73, 317, 318, 417, 356/346; 250/461.2, 461.1, 458.1; 382/6, 17; 364/413.08

[56] References Cited

U.S. PATENT DOCUMENTS

| | | | |
|---|---|---|---|
| 3,918,812 | 11/1975 | Holm | 356/73 |
| 4,125,828 | 11/1978 | Resnick et al. | 382/6 |
| 4,475,236 | 10/1984 | Hoffman | 382/6 |
| 4,661,913 | 4/1987 | Wu et al. | 382/6 |
| 4,786,813 | 11/1988 | Svanberg et al. | 250/458.1 |
| 4,802,762 | 2/1989 | Hill, Jr. | 356/417 |
| 4,905,169 | 2/1990 | Buican et al. | 364/525 |

Primary Examiner—Leo H. Boudreau
Assistant Examiner—Barry Stellrecht
Attorney, Agent, or Firm—Ray G. Wilson; Paul D. Gaetjens; William R. Moser

[57] ABSTRACT

An integrated fluorescence analysis system enables a component part of a sample to be virtually sorted within a sample volume after a spectrum of the component part has been identified from a fluorescence spectrum of the entire sample in a flow cytometer. Birefringent optics enables the entire spectrum to be resolved into a set of numbers representing the intensity of spectral components of the spectrum. One or more spectral components are selected to program a scanning laser microscope, preferably a confocal microscope, whereby the spectrum from individual pixels or voxels in the sample can be compared. Individual pixels or voxels containing the selected spectral components are identified and an image may be formed to show the morphology of the sample with respect to only those components having the selected spectral components. There is no need for any physical sorting of the sample components to obtain the morphological information.

4 Claims, 2 Drawing Sheets ic properties. The steps include inputting the actual sample to a flow cytometer to resolve the sample into a plurality of individual particles; exciting a fluorescence spectrum from each of the individual particles; resolving the fluorescence spectrum from each of the individual particles into a set of numbers representing the intensity of spectral components in the fluorescence spectrum; and storing the set of numbers in a storage location for access to reconstruct an image of the individual particles having preselected ones of the spectral components. The actual sample is then provided to a scanning microscope to scan the actual sample with a laser beam to excite a fluorescence spectrum over an image plane containing the individual particles. The fluorescence spectrum is resolved into a plurality of pixels over the image plane, each pixel having a pixel fluorescence with one or more spectral wavelengths. Each pixel fluorescence is then resolved into numbers representing the intensity of spectral components in the pixel fluorescence. The stored numbers are then accessed and the pixel numbers are compared with the stored numbers to output pixel numbers corresponding to the stored numbers for developing a pixel image over the image plane corresponding to the preselected spectrum.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 3 is a flow chart of one process for practicing the present invention using flow cytometer data to enhance selected fluorochrome spectra obtained in image cytometry.

FIG. 4 is a flow chart of one process for practicing the present invention using image cytometry data to enhance selected fluorochrome spectra obtained in flow cytometry.

DETAILED DESCRIPTION OF THE PREFERRED EMBODIMENTS

Figure 1:
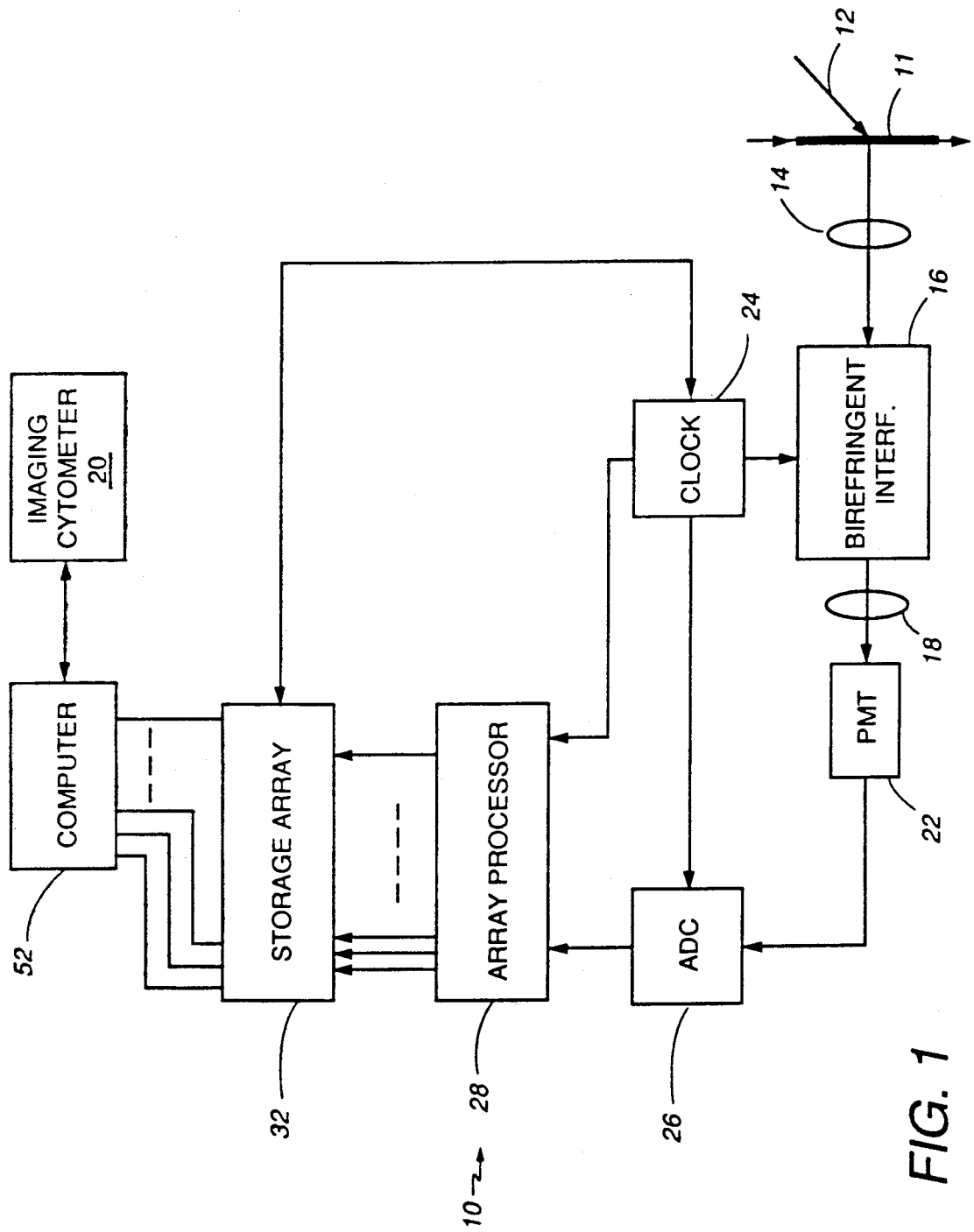
FIG. 1 is a schematic in block diagram form of an integrated fluorescence analysis system according to the present invention.

In accordance with the present invention, flow cytometry and image cytometry are integrated to obtain spectral information about a sample of interest and to enable further analysis to enhance selected spectra for enhanced imaging of selected cellular subpopulations. Referring now to FIG. 1, there is shown in general block diagram form an integrated flow-image cytometry system 10. Sample 12 is a conventional biological specimen, typically containing fluorochromes either naturally or provided by the analyst to label specific cellular components, as hereinabove discussed.

Sample 12 is provided to flow cytometer 16 for conventional hydrodynamic focusing to produce a single file stream of individual particles, e.g., cells. The particles are then excited by laser excitation beam 14 to produce a fluorescence spectrum. The fluorescence spectrum is then analyzed by processor 18 to provide output 22, where output 22 is typically a set of numbers describing the intensity of preselected spectral components of the fluorescence spectrum. In a preferred embodiment, processor 18 is a Fourier-Transform (FT) spectrometer which enables simultaneous processing of all desired spectral components using birefringent optics as taught in U.S. Pat. No. 4,905,169, incorporated herein by reference. As taught therein, the FT spectrometer inputs the fluorescence spectrum from each individual cell and resolves the spectrum into numbers representing the spectral components selected by the analyst.

Sample 12 is also provided as sample 24 to microscope 28. Microscope 28 is preferably a confocal microscope with a scanning capability for scanning laser beam 26 across an image plane on sample 24. Laser beam 26 then excites a fluorescence spectrum from each pixel in the image plane as the laser beam scans the image plane. The pixel fluorescence is then provided to processor 32 which generates output 36 as a set of numbers representing the intensity of selected spectral components. Again, processor 32 is preferably a FT spectrometer.

Figure 2:
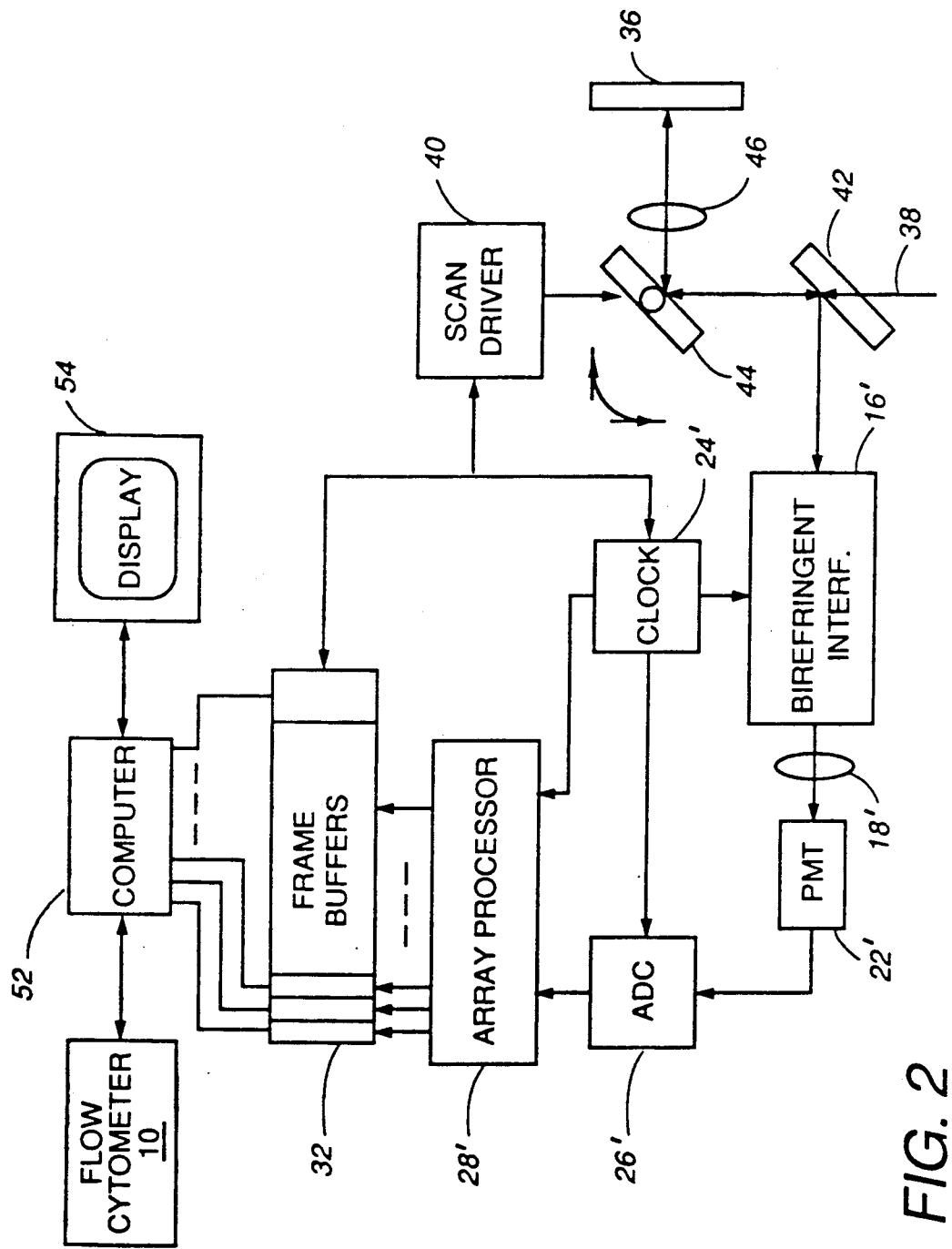
FIG. 2 is a block diagram of a spectral imaging cytometer using birefringent optics for parallel processing of spectral information.

The scanning and fluorescence detection by microscope 28 and processor 32 are more completely shown in FIG. 2. As shown in FIG. 2, laser beam 26 is directed by beam splitter 44 through objective 46 to scan sample 24. Fluorescence emissions from sample 24 are returned through objective 46 and beam splitter 44 to pinhole aperture 48 for confocal operation. The fluorescence is then input to FT spectrometer 32. Within FT spectrometer 32, the fluorescence is directed through birefringent optics 52, i.e., polarizer 54, birefringent plate assembly 56, and analyzer 58, onto photomultiplier tube 62. Birefringent plate assembly 56 functions to produce a plurality of retardations for processing a plurality of spectral components from the input fluorescence spectrum. Photomultiplier tube 62 is responsive to the plurality of spectral components and outputs 64 an interferogram to processor means 66. Processor 66 conventionally generates a Fourier-Transform to obtain output numbers 36 representing the intensity of the spectral components of the fluorescence from each pixel of sample 24.

Referring again to FIG. 1, output 22 is a set of numbers representing selected spectral components of the fluorescence from an individual particle in sample 12. Output 36 is a set of numbers representing spectral components of the fluorescence from a pixel in the image plane of sample 24. Selection process 38 applies outputs 22 and 36 to enhance the imaging of sample 24 through microscope 28. That is, outputs 22 are used to selectively enhance pixel fluorescence, i.e., outputs 36, for developing an enhanced image of sample 24 as output 42 from imaging device 34.

Outputs 22 can be provided as input 22a to imaging device 34 and used as discriminators to select outputs 36 for inclusion in imaging output 42. In tral components. The actual sample is irradiated with a laser beam to stimulate a fluorescence spectrum from the sample having one or more spectral wavelengths. The fluorescence spectrum is resolved into sample numbers representing the intensity of spectral components in the fluorescence spectrum. The sample numbers are compared with stored numbers representing the preselected spectral components. Portions of the sample are then identified that have a fluorescence spectrum corresponding with the preselected spectral components.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1 is a schematic in block diagram form of an integrated fluorescence analysis system according to the present invention particularly showing flow cytometry components.

FIG. 2 is a schematic in block diagram form of an integrated fluorescence analysis system according to the present invention particularly showing imaging cytometry components.

DETAILED DESCRIPTION OF THE INVENTION

In accordance with the present invention, a sample is irradiated with a laser beam to produce a fluorescence response spectrum having a plurality of wavelengths. Birefringent optics, as described in U.S. Pat. 4,905,169, incorporated by reference, enable a Fourier analysis to resolve the fluorescence spectrum into numbers representing the intensity of each of the spectral wavelengths of the fluorescence. Thus, a set of numbers representing base spectra can be selected from the total spectrum and thereafter used to provide virtual sorting of biological particles against the base spectra.

As shown in FIGS. 1 and 2, an integrated fluorescence analysis system incorporates a flow cytometer 10 and an imaging cytometer 20, each with birefringent optics, and communicating with one another through a communication channel, such as computer 52. Flow cytometer 10 and imaging cytometer 20 cooperate in the following ways: (a) base spectra for resolving total cell/pixel fluorescence are shared; and (b) the spectral data obtained by one instrument are used to program the other instrument. Then, if the analysis of a cell suspension reveals the existence of a spectrally distinct subpopulation, the average spectrum for that population can be transferred from one instrument to the other to enhance the cell/pixel data and identify cells/pixels that have the same spectral properties. In the imaging cytometer, an image can then be formed with only those pixels containing spectral features of interest. Conversely, the average spectrum of a whole cell of interest, or that of a particular morphological detail, can be transferred to the flow cytometer, where it is used to identify and quantitate cell subpopulations with the same spectral properties.

Referring now to FIG. 1, flow cytometer 10 communicates with imaging cytometer 20 through computer 52. Flow cytometer 10 provides for simultaneously measuring a plurality of spectral wavelengths present in fluorescence produced when a laser beam 12 excites sample materials, such as biological cells, contained in focused flow stream 11. The output fluorescence is input by lens 14 to birefringent interferometer 16, as particularly described in the '169 patent. It will be appreciated that the sample materials may be biological particles such as chromosomes or other cellular material. The particles can be unstained, wherein the fluorescence is intrinsic fluorescence or autofluorescence, or stained with one or more fluorochromes.

Interferometer 16 includes birefringent elements and polarizing elements to introduce a time-varying phase difference between spectral components of the output fluorescence. Detector 22, which may be a photomultiplier tube (PMT), produces an electrical output signal characteristic of the sum of the intensities of the spectral components incident on detector 22. Analog-to-digital (ADC) converter 26 digitizes the electrical signals output from detector 22 for input to array processor 28. Clock 24 is phase-locked with interferometer 16 and synchronizes operation of the system elements. Clock 24 strobes ADC 26, processor 28, and storage array 32 at a frequency that is greater than the frequency at which birefringent interferometer 16 is driven.

Array processor 28 receives the output from ADC 26 for processing. Processor 28 includes a multiplicity of processors equal to the number of spectral channels over which the fluorescence is to be measured. Each processor computes and outputs a single number representing the intensity of one spectral channel, or wavelength, of the fluorescence from samples in flow stream 11. Storage array 32 then stores the computed spectral numbers. Computer 52 enables imaging cytometer 20 to communicate with storage array 32, as hereinafter discussed.

Referring now to FIG. 2, there is shown a block diagram schematic of an imaging cytometer according to the present invention. It will be understood that the optical analyzing elements, i.e., birefringent interferometer 16', lens 18', detector 22', array processor 28', and clock 24' are identical with the corresponding components 16, 18, 22, 28, and 24 discussed in FIG. 1. A scanning laser microscope 38, 40, 42, 44, and 46 provides the optical input to interferometer 16'. A confocal scanning microscope, e.g., a BioRad MRC-500, can scan over a plurality of image planes within sample 36 to develop a three dimensional image.

Laser beam 38 is input through dichroic mirror 42 to scanning mirror 44, which is driven by scan driver 40 to traverse beam 38 through optics 46 over an image plane within specimen 36. Fluorescence excited from specimen 36 is transmitted to interferometer 16' through microscope lens 46, scanning mirror 44, and dichroic mirror 42. The fluorescence data from specimen 36 is provided as pixel information for a given image plane, i.e., scan driver 40 is synchronized through clock 24' so that fluorescence data are obtained from a sequence of discrete locations over the image plane within specimen 36. It will be appreciated that the fluorescence spectrum from each pixel will be a composite spectrum, i.e., one or more wavelengths, from the fluorescent components in the pixel area. It will also be appreciated that the confocal microscope can scan image planes through the entire volume of a sample so that each "pixel" represents a volume, or "voxel.+ The term "pixel" will be used herein to mean a focal region for scanning microscope 45, whether on a surface area or within a sample volume.

The output from array processor 28' is a set of numbers representing the spectral components of each pixel fluorescence. In one embodiment of the present invention, computer 52 communicates with flow cytometer 10 to obtain one or more numbers indicative of a selected spectral component of specimen 36. As the spectral component numbers from specimen 36 are presented to frame buffers 48, computer 52 selects only those pixels having the selected spectral component or components. The image that is generated for display 54 contains only those pixels having the desired spectral components, i.e., only the desired characteristics such as a particular chromosome or cell or undergoing a particular chemical reaction that produces the selected spectral component or components.

Thus, flow cytometer 10 may examine a serial flow of samples to determine the spectral components of a particular sample of interest. These spectral components are communicated to computer 52 and thereafter used to form the image that is displayed from image cytometer 20 as specimen 36 is scanned by laser beam 38. As a sample is scanned, those pixels having the selected spectral components are enhanced in brightness wherein all cells or subcellular structures with the desired spectral properties appear bright, while all other details appear as a dim background. This difference in intensity allows the identification of those cells that belong to the subpopulation identified in flow cytometry and the analysis of their morphology.

This image enhancement is a "virtual sorting" of the sample components having the selected spectral characteristics. It is equivalent in its results to physical sorting followed by microscopic examination, with the major difference that, in the case of virtual sorting, one sorts numerical data rather than actual cells. Apart from not requiring a physical sorting capability on the flow cytometer, nor the collection of sorted cells and the preparation of separate microscopy samples for each subpopulation of interest, virtual sorting allows large numbers of subpopulations to be analyzed simultaneously from a morphological point of view. The number of simultaneously analyzed subpopulations is limited only by the number of channels in the data processing system of the FT imaging cytometer and by the spectral resolution of the FT spectrometers (typically eight or more), and can exceed by far the number of subpopulations that can be simultaneously physically sorted (typically two to four).

In a "reversed" virtual sorting, the spectral properties of morphologically interesting cells are communicated from image cytometer 20 to flow cytometer 10 to program the FT flow cytometer. In this case, the flow cytometer would rapidly provide population-level data on the abundance of the cells or cellular components of interest. The spectral properties can also be used to program an optical trapping system, such as taught by U.S. Pat. No. 4,887,721, issued Dec. 19, 1989, to separate cells identified as having the same spectral properties as the subpopulation of interest. This technique, an "indirect sorting", is useful when the staining properties of a subpopulation of rare cells are only approximately known, but can be accurately and rapidly determined in flow. Then, the imaging cytometer can accurately discriminate between the rare cells of interest and the rest of the sample, and the automated optical trapping system can scan through the sample, identify the cells, and separate them.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An integrated fluorescence analysis system, comprising:
   flow cytometer means having birefringent optics for measuring a first plurality of simultaneous spectral wavelengths present in a first fluorescence spectrum from a first sample;
   first processor means for resolving said first fluorescence spectrum into first numbers representing the intensity of spectral components of said first plurality of spectral wavelengths;
   an imaging cytometer having birefringent optics for measuring a second plurality of simultaneous spectral wavelengths present in a second fluorescence spectrum from a second sample;
   second processor means for resolving said second fluorescence spectrum into second numbers representing the intensity of spectral components of said second plurality of spectral wavelengths; and
   means connecting said first processor means with said second processor means for inputting said first numbers to said second processor and said second numbers to said first processor for respectively enhancing spectral components of said second and said first samples.

2. An integrated fluorescence analysis system according to claim 1, further including:
   scanning means for measuring said second plurality of spectral wavelengths at discrete pixel locations over a surface of said second sample; and
   computer display means for generating an image of said pixels having said second numbers enhanced by said first numbers from said flow cytometer.

3. An integrated fluorescence analysis system according to claim 1, wherein said imaging cytometer further includes:
   microscope means for scanning a laser beam over a selected sample image plane of said second sample to excite said second fluorescence spectrum over said surface;
   birefringent optics for resolving said second fluorescence spectrum into a plurality of pixels, each pixel having a pixel fluorescence with one or more spectral wavelengths;
   wherein said second processor resolves each said pixel fluorescence into said second numbers representing the intensity of spectral components is said pixel fluorescence;
   storage means for storing said first number representing the intensity of spectral components from said first spectrum; and
   means for selecting pixels having numbers corresponding to said stored second numbers to develop an image over said image plane corresponding to only pixels with said first spectrum.

4. An integrated fluorescence analysis system according to claim 3, wherein said microscope means is a confocal microscope.

* * * * *